(12) United States Patent
Siniaguine et al.

(10) Patent No.: US 7,253,435 B2
(45) Date of Patent: Aug. 7, 2007

(54) PARTICLES WITH LIGHT-POLARIZING CODES

(75) Inventors: Oleg Siniaguine, San Carlos, CA (US); Michael A. Zarowitz, San Carlos, CA (US); Ilya Ravkin, Palo Alto, CA (US)

(73) Assignee: Millipore Corporation, Billerica, MA (US)

( * ) Notice: Subject to any disclaimer, the term of this patent is extended or adjusted under 35 U.S.C. 154(b) by 112 days.

(21) Appl. No.: 10/713,866

(22) Filed: Nov. 14, 2003

(65) Prior Publication Data

US 2004/0096911 A1 May 20, 2004

Related U.S. Application Data

(63) Continuation-in-part of application No. 10/282,904, filed on Oct. 28, 2002, and a continuation-in-part of application No. 10/273,605, filed on Oct. 18, 2002, which is a continuation-in-part of application No. 10/120,900, filed on Apr. 10, 2002, and a continuation-in-part of application No. 09/549,970, filed on Apr. 14, 2000, now abandoned, and a continuation-in-part of application No. 09/694,077, filed on Oct. 19, 2000, said application No. 09/694,077 is a continuation-in-part of application No. 09/549,970, said application No. 10/282,904 and a continuation-in-part of application No. 09/694,077, is a continuation-in-part of application No. 10/120,900.

(60) Provisional application No. 60/426,633, filed on Nov. 14, 2002, provisional application No. 60/413,675, filed on Sep. 24, 2002, provisional application No. 60/359,207, filed on Feb. 21, 2002, provisional application No. 60/343,682, filed on Oct. 26, 2001, provisional application No. 60/344,482, filed on Oct. 26, 2001, provisional application No. 60/345,606, filed on Oct. 26, 2001, provisional application No. 60/244,483, filed on Oct. 26, 2001, provisional application No. 60/348,025, filed on Oct. 26, 2001, provisional application No. 60/241,714, filed on Oct. 18, 2000, provisional application No. 60/170,947, filed on Dec. 15, 1999, provisional application No. 60/129,664, filed on Apr. 15, 1999.

(51) Int. Cl.
*H01L 23/58* (2006.01)
(52) U.S. Cl. .............................. 257/48; 257/79; 436/6
(58) Field of Classification Search ................ 257/922, 257/48, 79
See application file for complete search history.

(56) References Cited

U.S. PATENT DOCUMENTS 3,772,099 A  11/1973  Ryan et al.

(Continued)

FOREIGN PATENT DOCUMENTS

GB  2 306 484  7/1997

(Continued)

OTHER PUBLICATIONS

*Generation and Screening of an Oligonucleotide-Encoded Synthetic Peptide Library*, Proc. Natl. Acad. Sci. USA, vol. 90, pp. 10700-10704, Nov. 1993.

(Continued)

*Primary Examiner*—Sara Crane
(74) *Attorney, Agent, or Firm*—Kolisch Hartwell, P.C.

(57) ABSTRACT

Systems using coded particles for multiplexed analysis of biological samples or reagents, in which the codes on the particles are at least partially defined by light-polarizing materials.

16 Claims, 4 Drawing Sheets

U.S. PATENT DOCUMENTS

| | | |
|---|---|---|
| 3,897,284 A | 7/1975 | Livesay |
| 3,964,294 A | 6/1976 | Shair et al. |
| 4,053,433 A | 10/1977 | Lee |
| 4,131,064 A | 12/1978 | Ryan et al. |
| 4,197,104 A | 4/1980 | Krystyniak et al. |
| 4,329,393 A | 5/1982 | LaPerre et al. |
| 4,363,965 A | 12/1982 | Soberman et al. |
| 4,469,623 A | 9/1984 | Danielson et al. |
| 4,544,836 A * | 10/1985 | Galvin et al. ............... 235/487 |
| 4,640,035 A | 2/1987 | Kind et al. |
| 4,652,395 A | 3/1987 | Marcina et al. |
| 5,143,854 A | 9/1992 | Pirrung et al. |
| 5,202,265 A | 4/1993 | LaMora |
| 5,409,839 A | 4/1995 | Balestrieri |
| 5,451,505 A | 9/1995 | Dollinger |
| 5,563,583 A | 10/1996 | Brady et al. |
| 5,581,257 A | 12/1996 | Greene et al. |
| 5,688,696 A | 11/1997 | Lebl |
| 5,708,153 A | 1/1998 | Dower et al. |
| 5,741,462 A | 4/1998 | Nova et al. |
| 5,744,305 A | 4/1998 | Fodor et al. |
| 5,751,629 A | 5/1998 | Nova et al. |
| 5,760,394 A | 6/1998 | Welle |
| 5,770,455 A | 6/1998 | Cargill et al. |
| 5,773,224 A | 6/1998 | Grandics et al. |
| 5,786,626 A | 7/1998 | Brady et al. |
| 5,817,751 A | 10/1998 | Szardenings et al. |
| 5,840,485 A | 11/1998 | Lebl et al. |
| 5,846,719 A | 12/1998 | Brenner et al. |
| 5,874,214 A | 2/1999 | Nova et al. |
| 5,874,724 A | 2/1999 | Cato |
| 5,925,562 A | 7/1999 | Nova et al. |
| 5,961,923 A | 10/1999 | Nova et al. |
| 5,981,166 A | 11/1999 | Mandecki |
| 5,981,180 A | 11/1999 | Chandler et al. |
| 5,989,835 A | 11/1999 | Dunlay et al. |
| 5,990,479 A | 11/1999 | Weiss et al. |
| 6,017,496 A | 1/2000 | Nova et al. |
| 6,018,299 A | 1/2000 | Eberhardt |
| 6,025,129 A | 2/2000 | Nova et al. |
| 6,025,200 A | 2/2000 | Kaish et al. |
| 6,046,003 A | 4/2000 | Mandecki |
| 6,051,377 A | 4/2000 | Mandecki |
| 6,083,693 A | 7/2000 | Nandabalan et al. |
| 6,083,763 A | 7/2000 | Balch |
| 6,093,370 A | 7/2000 | Yasuda et al. |
| 6,100,026 A | 8/2000 | Nova et al. |
| 6,100,973 A | 8/2000 | Lawandy |
| 6,103,479 A | 8/2000 | Taylor |
| 6,104,038 A | 8/2000 | Gonzalez et al. |
| 6,114,038 A | 9/2000 | Castro et al. |
| 6,129,896 A | 10/2000 | Noonan et al. |
| 6,136,274 A | 10/2000 | Nova et al. |
| 6,210,910 B1 | 4/2001 | Walt et al. |
| 6,214,560 B1 | 4/2001 | Yguerabide et al. |
| 6,238,869 B1 | 5/2001 | Kris et al. |
| 6,251,691 B1 | 6/2001 | Seul |
| 6,274,323 B1 | 8/2001 | Bruchez et al. |
| 6,296,189 B1 | 10/2001 | Lawandy et al. |
| 6,306,975 B1 | 10/2001 | Zhao et al. |
| 6,326,144 B1 | 12/2001 | Bawendi et al. |
| 6,908,737 B2 * | 6/2005 | Ravkin et al. ............... 435/6 |
| 2002/0123078 A1 | 9/2002 | Seul et al. |
| 2003/0129654 A1* | 7/2003 | Ravkin et al. ............... 435/7.1 |
| 2003/0134330 A1* | 7/2003 | Ravkin et al. ............... 435/7.1 |
| 2003/0157730 A1 | 8/2003 | Walker et al. |
| 2004/0038306 A1 | 2/2004 | Agnew et al. |

FOREIGN PATENT DOCUMENTS

| | | |
|---|---|---|
| WO | WO 96/36436 | 11/1996 |
| WO | WO 97/12680 | 4/1997 |
| WO | WO 97/20074 | 6/1997 |
| WO | WO 97/35201 | 9/1997 |
| WO | WO 98/46550 | 10/1998 |
| WO | WO 98/53093 | 11/1998 |
| WO | WO 99/19515 | 4/1999 |
| WO | WO 99/22018 | 5/1999 |
| WO | WO 99/36564 | 7/1999 |
| WO | WO 99/37814 | 7/1999 |
| WO | WO 99/41006 | 8/1999 |
| WO | WO 99/67641 | 12/1999 |
| WO | WO 00/00145 | 1/2000 |
| WO | WO 00/22435 | 4/2000 |
| WO | WO 00/32542 | 6/2000 |
| WO | WO 00/33079 | 6/2000 |
| WO | WO 00/39587 | 6/2000 |
| WO | WO 00/73777 | 12/2000 |
| WO | WO 01/25002 | 4/2001 |
| WO | WO 01/25510 | 4/2001 |
| WO | WO 01/61040 | 8/2001 |
| WO | WO 01/77391 | 10/2001 |
| WO | WO 01/78288 | 10/2001 |
| WO | WO 01/89585 | 11/2001 |
| WO | WO 01/96604 | 12/2001 |
| WO | WO 01/98765 | 12/2001 |

OTHER PUBLICATIONS

*Strategies and Techniques in Simultaneous Solid Phase Synthesis Based on the Segmentation of Membrane Type Supports*, Bioorganic & Medicinal Chemistry Letters, vol. 3, No. 3, pp. 425-430, 1993.
*Nanowires Formed in Anodic Oxide Nanotemplates*, J. Mater. Res., vol. 9, No. 4, pp. 1014-1018, Apr. 1994.
*Membrane-Based Synthesis of Nanomaterials*, Chem. Mater., vol. 8, No. 8, pp. 1739-1746, 1996.
*Symposium BB Nonlithographic Methods for Organizing Materials into Functional Structures*, pp. 1-9, Nov. 30-Dec. 2, 1998.
*Orthogonal Self-Assembly on Colloidal Gold-Platinum Nanorods*, Adv. Mater., vol. 11, No. 12, pp. 1021-1025, 1999.
*Symposium C Anisotropic Nanoparticles—Synthesis, Characterization, and Applications*, pp. 54-69, Nov. 27-29, 2000.
*Rational Design of Cytophilic and Cytophobic Polyelectrolyte Multilayer Thin Films*, Mendelsohn et al., *Biomacromolecules*, vol. 4, No. 1, pp. 96-106, 2003.

* cited by examiner

PARTICLES WITH LIGHT-POLARIZING CODES

CROSS-REFERENCES TO PRIORITY APPLICATIONS

This application is a continuation-in-part of the following U.S. patent applications: Ser. No. 10/273,605, filed Oct. 18, 2002; and Ser. No. 10/282,904, filed Oct. 28, 2002. This application also is based upon and claims the benefit under 35 U.S.C. § 119(e) of U.S. Provisional Patent Application Ser. No. 60/426,633, filed Nov. 14, 2002, which is incorporated herein by reference in its entirety for all purposes.

U.S. patent application Ser. No. 10/273,605, in turn, is a continuation-in-part of the following U.S. patent applications: Ser. No. 09/549,970, filed Apr. 14, 2000; Ser. No. 09/694,077, filed Oct. 19, 2000; and Ser. No. 10/120,900, filed Apr. 10, 2002. The '605 application also is based upon and claims the benefit under 35 U.S.C. § 119(e) of the following U.S. provisional patent applications: Ser. No. 60/343,682, filed Oct. 26, 2001; Ser. No. 60/343,685, filed Oct. 26, 2001; Ser. No. 60/344,482, filed Oct. 26, 2001; Ser. No. 60/344,483, filed Oct. 26, 2001; Ser. No. 60/345,606, filed Oct. 26, 2001; Ser. No. 60/359,207, filed Feb. 21, 2002; and Ser. No. 60/413,675, filed Sep. 24, 2002.

U.S. patent application Ser. No. 09/549,970, in turn, is based upon and claims the benefit under 35 U.S.C. § 119(e) of the following U.S. provisional patent applications: Ser. No. 60/129,664, filed Apr. 15, 1999; and Ser. No. 60/170,947, filed Dec. 15, 1999.

U.S. patent application Ser. No. 09/694,077, in turn, is a continuation-in-part of U.S. patent application Ser. No. 09/549,970 (with priority claims as indicated above). The '077 application also is based upon and claims the benefit under 35 U.S.C. § 119(e) of U.S. Provisional Application Ser. No. 60/241,714, filed Oct. 18, 2000.

U.S. patent application Ser. No. 10/120,900, in turn, claims the benefit under 35 U.S.C. § 120 of PCT Application Ser. No. PCT/US01/51413, filed Oct. 18, 2001, and published in English as Publication No. WO 02/37944 on May 16, 2002, which in turn is based upon and claims the benefit under 35 U.S.C. § 119(e) of the following U.S. provisional patent applications: Ser. No. 60/241,714, filed Oct. 18, 2000; Ser. No. 60/259,416, filed Dec. 28, 2000; Ser. No. 60/293,863, filed May 24, 2001; Ser. No. 60/299,267, filed Jun. 18, 2001; Ser. No. 60/299,810, filed Jun. 20, 2001; Ser. No. 60/307,649, filed Jul. 24, 2001; Ser. No. 60/307,650, filed Jul. 24, 2001; Ser. No. 60/310,540, filed Aug. 6, 2001; Ser. No. 60/317,409, filed Sep. 4, 2001; Ser. No. 60/318,156, filed Sep. 7, 2001; and Ser. No. 60/328,614, filed Oct. 10, 2001.

U.S. patent application Ser. No. 10/282,904, in turn, is a continuation-in-part of U.S. patent application Ser. No. 09/694,077 filed Oct. 19, 2000 (with priority claims as indicated above), and U.S. patent application Ser. No. 10/120,900, filed Apr. 10, 2002 (with priority claims as indicated above). The '904 application also is based upon and claims the benefit under 35 U.S.C. § 119(e) of U.S. Provisional Patent Application Ser. No. 60/348,025, filed Oct. 26, 2001.

CROSS-REFERENCES TO ADDITIONAL APPLICATIONS

This application incorporates by reference in their entirety for all purposes the following U.S. patent applications: Ser. No. 09/549,970, filed Apr. 14, 2000; Ser. No. 09/694,077, filed Oct. 19, 2000; Ser. No. 10/120,900, filed Apr. 10, 2002; Ser. No. 10/238,914, filed Sep. 9, 2002; Ser. No. 10/273,605, filed Oct. 18, 2002; Ser. No. 10/282,904, filed Oct. 28, 2002; and Ser. No. 10/282,940, filed Oct. 28, 2002.

This application also incorporates by reference in their entirety for all purposes the following U.S. provisional patent applications: Ser. No. 60/343,682, filed Oct. 26, 2001; Ser. No. 60/343,685, filed Oct. 26, 2001; Ser. No. 60/344,482, filed Oct. 26, 2001; Ser. No. 60/344,483, filed Oct. 26, 2001; Ser. No. 60/345,606, filed Oct. 26, 2001; Ser. No. 60/348,025, filed Oct. 26, 2001; Ser. No. 60/359,207, filed Feb. 21, 2002; Ser. No. 60/362,001, filed Mar. 5, 2002; Ser. No. 60/362,055, filed Mar. 5, 2002; Ser. No. 60/362,238, filed Mar. 5, 2002; Ser. No. 60/370,313, filed Apr. 4, 2002; Ser. No. 60/383,091, filed May 23, 2002; Ser. No. 60/383,092, filed May 23, 2002; Ser. No. 60/413,407, filed Sep. 24, 2002; Ser. No. 60/413,675, filed Sep. 24, 2002; and Ser. No. 60/421,280, filed Oct. 25, 2002.

FIELD OF THE INVENTION

The invention relates to systems using coded particles. More particularly, the invention relates to systems using coded particles for multiplexed analysis of biological samples or reagents, in which the codes on the particles are at least partially defined by light-polarizing materials.

BACKGROUND OF THE INVENTION

Coded particles enable formation of positionally flexible arrays for multiplexed analysis of samples and reagents. Such coded particles may include a code portion and an assay portion. The code portion defines an optically detectable code for tracking and identifying each particle in a mixture of particles. The assay portion provides a region for performing an assay and for detecting an optical outcome of the assay. Accordingly, the code and assay portions should not interfere optically with one another. One approach to avoid optical interference is to spatially segregate the code and assay portions, so that each may be detected separately. However, spatial segregation may not be sufficient in some cases, for example, when the code and assay portions have similar optical properties. In addition, spatial segregation may be undesirable because it increases the size of the particles or reduces the space on each particle for performing assays.

SUMMARY OF THE INVENTION

The invention provides systems using coded particles for multiplexed analysis of biological samples or reagents, in which the codes on the particles are at least partially defined by light-polarizing materials.

DETAILED DESCRIPTION OF THE INVENTION

Systems, including methods, apparatus, kits, and compositions, are provided for multiplexed analysis using coded particles having codes defined at least partially by light-polarizing material. Light-polarizing material may facilitate forming a polarization code that is detectable with polarized and/or nonpolarized light. Accordingly, polarization codes may be detected with polarized light but may be substantially transparent for multiplexed analysis of samples using nonpolarized light. Therefore, polarization codes may produce less optical interference when detecting assay results. As a result, polarization codes may be disposed in an overlapping relationship with an assay portion of each particle, thereby providing a larger region for sample analysis on the particle.

Figure 1:
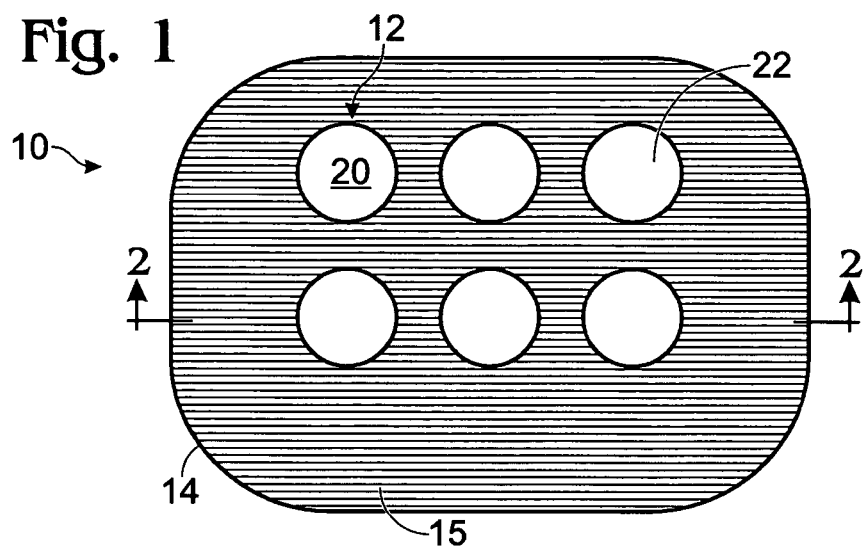
FIG. 1 is a top plan view of a particle having a polarization code defined by a light-polarizing material, in accordance with aspects of the invention.
Figure 2:
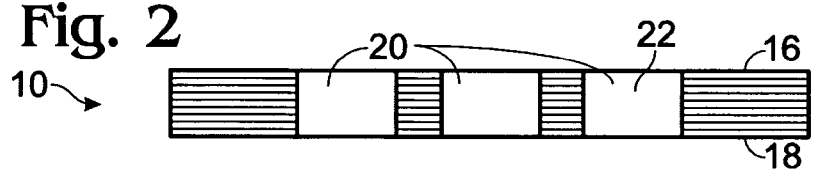
FIG. 2 is a sectional view of the particle of FIG. 1 taken generally along line 2-2 in FIG. 1.

FIGS. 1 and 2 shows plan and sectional views, respectively, of a particle 10 having an optical code 12 defined by the distribution of a light-polarizing material. Particle 10 includes a substrate 14 made of, or including, material 15 with linear light-polarizing properties. Substrate 14 may have flat surfaces 16, 18 to form a generally planar particle with a rectangular cross-sectional shape. Alternatively, substrate 14 may have any other suitable cross-sectional or three-dimensional shape. For exemplary purposes, a substrate of a generally rectangular shape with rounded corners is shown. Further aspects of particle shapes, sizes, materials, and surfaces that may be suitable are described in more detail in the patents and patent applications identified in the Cross-References and incorporated herein by reference, particularly U.S. patent application Ser. No. 10/273,605, filed Oct. 18, 2002.

Any suitable material having linear light-polarizing properties may be used in particle 10. In some embodiments, the polarizing material has optical properties that do not interfere with optical analysis of sample characteristics using non-polarized light. For example, the polarizing material may Show little fluorescence or absorbance at the wavelength at which assay results are detected. Alternatively, or in addition, as described below, the polarizing material may be restricted to a coding portion of the particle. An exemplary polarizing material is a synthetic linear-polarizing material with aligned long-chain polymers, such as polyvinylene, which is manufactured by 3M, Inc., and which has part number HN-32.

Code 12 of particle 10 may be defined by nonpolarizing regions 20 of substrate 14. Each nonpolarizing region 20 may define a code element 22 of code 12, for example, based on the number, position, shape, size, etc. of the nonpolarizing region. In other embodiments, code elements 22 may be able to polarize light, while other regions of substrate 14 may lack the ability to polarize light. Furthermore, polarizing or nonpolarizing code elements may be combined with optically distinct code elements, such as code elements that absorb, emit, reflect, and/or refract light distinctively, among others. Further aspects of suitable codes and code elements that may be defined by polarizing and nonpolarizing regions alone, or in combination with other code elements, are described in more detail in the patents and patent applications identified in the Cross-References and incorporated herein by reference, particularly U.S. patent application Ser. No. 10/273,605, filed Oct. 18, 2002.

Code 12 may be fabricated by localized modification of the light-polarizing properties of substrate 14. Such modification may be achieved by localized removal of substrate material. Alternatively, or in addition, the modification may be carried out by randomizing the orientation of, and/or at least partial destruction of, polymers that constitute the polarizing material. Exemplary techniques for localized modification may include dry or wet etching, or laser ablation, among others.

Figure 3:
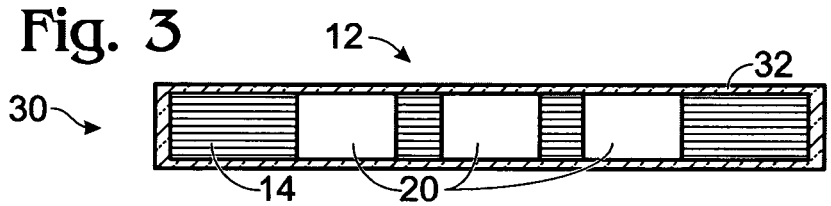
FIG. 3 is sectional view of a particle with a polarization code that is covered by a cladding, in accordance with aspects of the invention.

FIG. 3 shows a sectional view of another particle 30 having a code 12 defined by light-polarizing material. Particle 30 may include a cladding 32 that covers one or more surfaces, or all surfaces, of substrate 14. Cladding 32 may provide, for example, protection from mechanical and/or chemical damage, and/or may impart strength or structural rigidity, among others, to particle 30. Material used to form cladding 32 may lack polarizing properties and may be optically transparent or at least optically noninterfering when reading the code and/or measuring assay results.

Figure 4:
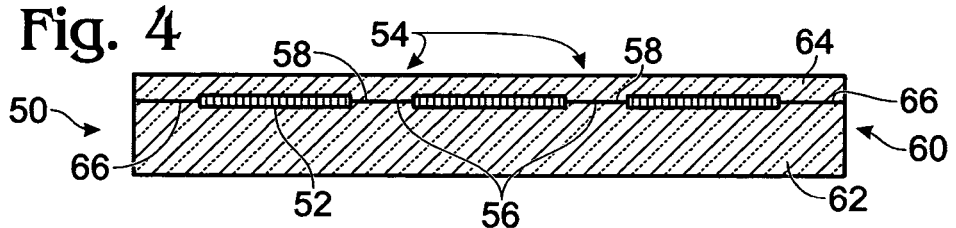
FIG. 4 is a sectional view of a particle with a patterned polarization layer supported between a substrate and a cladding layer, in accordance with aspects of the invention.

FIG. 4 shows a particle 50 having a patterned film or layer 52 with light-polarizing properties to define a code 54 having code elements 56. Code 54 may be defined by removing or depolarizing selected regions, such as region 58 of polarizing layer 52, to define code elements 56.

Particle 50 may include a support structure 60 on or in which polarizing layer 52 is attached or embedded. Here, support structure 60 includes a substrate 62 upon which polarizing layer 52 is formed and/or attached. In some embodiments, a cover or cladding layer 64 may be attached to substrate 62 to substantially enclose and protect polarizing layer 52. Cover 64 may form a flat or planar surface to planarize the particle above polarizing layer 52. This may compensate for unevenness produced by patterning polarizing layer 52. The cover may be formed of a material that is similar to, or distinct from, substrate 62 and/or cladding 32 (see FIG. 3). Substrate 62 and/or cover 64 may be formed of a material with suitable optical properties, such as low light absorption in the wavelength range used for reading codes and/or measuring sample characteristics. Suitable substrate materials may include glass, plastic (PMMA, PEMA, etc.), and/or the like. Other substrate materials that may be suitable are described in more detail in the patents and patent applications identified in the Cross-References and incorporated herein by reference, particularly U.S. patent application Ser. No. 10/273,605, filed Oct. 18, 2002.

Material to form polarizing layer 52 may have linear polarization properties in the wavelength range of visible light used for coded particle detection, and low light absorption in other wavelength ranges. As an example, a thin-film polarizing material, Black or Violet LCP, may be used. Black or Violet LCP is based on self-orienting sulfonated dye molecules and is produced by Optiva, Inc. (San Francisco, USA). The code pattern in polarizing layer 52 may be fabricated by localized modification of the layer's light-polarizing properties, as described above for particle 10 of FIGS. 1 and 2.

In some embodiments, particles with polarizing codes may include plural layers of material With light-polarizing properties. For example, one or more additional polarizing layers may be located over a first polarizing layer, over a cladding layer disposed over the first polarizing layer, and/or on a surface of the substrate that opposes the surface on which the first polarizing layer is disposed. These additional polarizing layers may be patterned as described above for particle 10. In some embodiments, plural polarizing layers may be patterned simultaneously, for example, when laser ablation is used for patterning.

The polarizing plane of additional polarizing layers may be oriented as suitable relative to the polarizing plane of the first polarizing layer. In some embodiments, the polarizing plane of a second polarizing layer may be substantially parallel to the polarizing plane of the first polarizing layer. This arrangement may improve the accuracy of reading the code, because the second polarizing layer may minimize transmission of nonpolarized light due to imperfections in the first polarizing layer caused by physical or manufacturing defects, such as pores, pinholes, particles, scratches, etc. Accordingly, the transmission of nonpolarized light from a double layer of similarly oriented polarizing material may be reduced significantly. In other embodiments, the polarizing plane of a second polarizing layer may be oriented substantially perpendicular to the polarizing plane of the first polarizing layer. In these cases, the particle may exhibit high optical contrast in transmitted light because the two layers may substantially block all light transmission at wavelengths for which the polarizing layers are effective. Furthermore, code elements at positions where both layers have been removed or modified may be detected independent of particle orientation and without the use of polarized light. However, if the light-blocking double layer is included in the assay portion of the particle, sample detection only may be possible from one side of the particle, for example, by fluorescence excitation/emission. This limitation may affect sensitivity or flexibility of sample analysis.

A second polarizing layer may be protected by a first or second cladding layer or cover, as described above for FIG. 4. The outer surface of the cladding layer may define a flat exterior surface, so that the cladding layer is planarized.

In some embodiments, a polarizing layer may not extend to an edge of the particle. For example, polarizing material of polarizing layer 52 is spaced from the edge of particle 50, as shown at 66 (see FIG. 4). This arrangement may promote hermetic and/or fluidic sealing of polarizing layer 52 by support structure 60 and may provide more reliable and robust protection from harmful ambient conditions.

In some embodiments, at least one polarizing or cladding layer may be colored. Such a colored layer may help to distinguish different types of particles visually and/or may contribute to the code.

Coded particles with polarization codes may have any suitable dimensions. In some embodiments, the substrate may have a thickness of about 0.01-1 mm, the polarizing layer(s) a thickness of about 0.1-100 microns, and the cladding layer(s) a thickness of about 1-300 microns.

Figure 5:
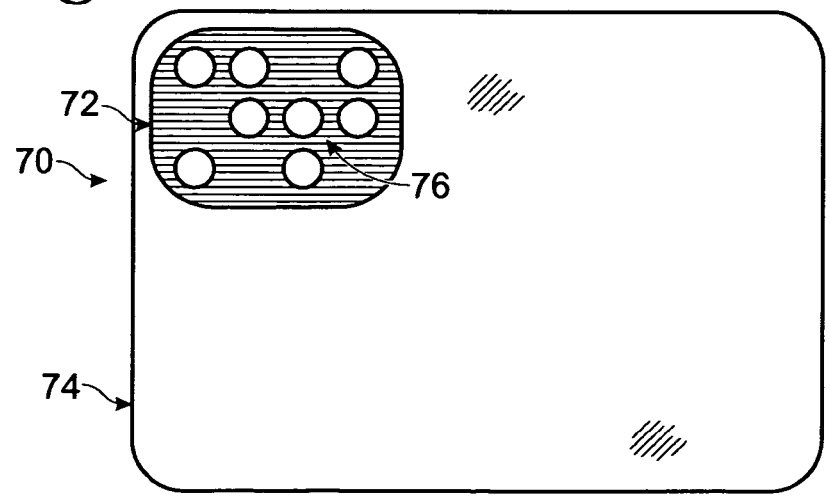
FIG. 5 is a plan view of a polarization-coded particle having a coding portion that is polarizing and a distinct noncoding portion that is nonpolarizing, in accordance with aspects of the invention.

FIG. 5 shows a particle 70 having a light-polarizing coding portion 72 and a noncoding portion 74 that does not polarize light. Coding portion 72 may occupy only a subset of particle 70 to define code 76. Accordingly, only a portion of the particle may show polarization-dependent optical properties. Assay results may be detected from the whole particle or only from noncoding portion 74. Coding and noncoding portions or regions are described in more detail in the patents and patent applications identified in the Cross-References and incorporated herein by reference, particularly U.S. patent application Ser. No. 10/273,605, filed Oct. 18, 2002.

FIG. 6 shows an exemplary method for fabricating particles having polarization codes. Individual particles may be fabricated on separate substrates, or plural particles may be produced together using a progenitor sheet that is cut or otherwise divided to form plural individual particles, termed singulation. The latter method may be more effective for mass production of the particles, and, thus, exemplary manufacturing intermediates for such a method are depicted in FIGS. 6A-F.

Figure 6A:
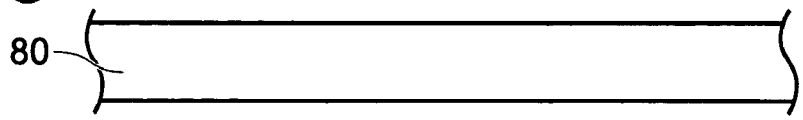
FIGS. 6A-F are fragmentary sectional views of a support plate (A), intermediate structures (B-E), and final particles (F) produced using a method for fabricating plural particles having polarization codes, in accordance with aspects of the invention.

FIG. 6A shows a plate 80 that may be used to support particle intermediates on a planar surface of the plate during particle fabrication. An exemplary material for plate 80 is glass or steel, although any suitable materials may be used.

Figure 6B:
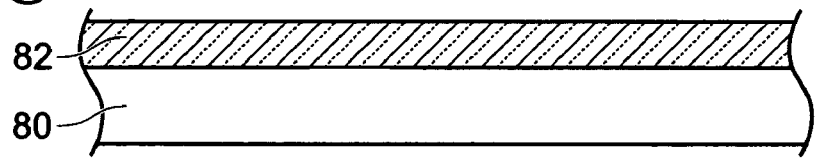

FIG. 6B shows a substrate sheet 82 supported by plate 80. Materials for substrate sheet 82 (such as PMMA, PEMA, etc.) may be applied to plate 80, for example, by laminating a film or drawing a liquid material (such as a melted material or a prepolymer solution). When applied as a liquid, the liquid may be dried, solidified, and/or cured following application. Accu-Lab Drawdown Machine, Part# DP-1240, manufactured by Paul N. Gardner Company, Inc., may be used for forming and/or applying substrate sheet 82.

Figure 6C:
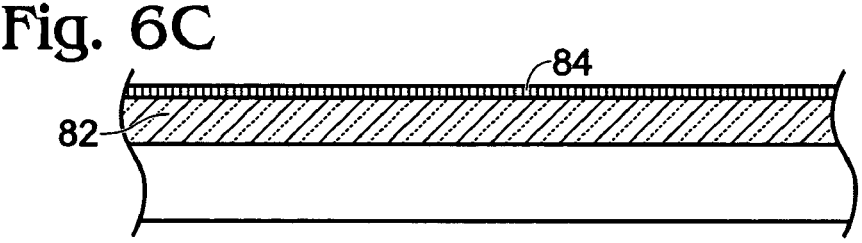

FIG. 6C shows substrate sheet 82 after application of a layer 84 of polarizing material. Polarizing layer 84 may be applied on a top surface of substrate sheet 82 by any suitable method, including lamination of a polarizing material sheet (e.g., 3M, Inc.) and/or by application of liquid polarizing material (e.g., Optiva, Inc.), followed by drying, solidifying, and/or curing.

Figure 6D:
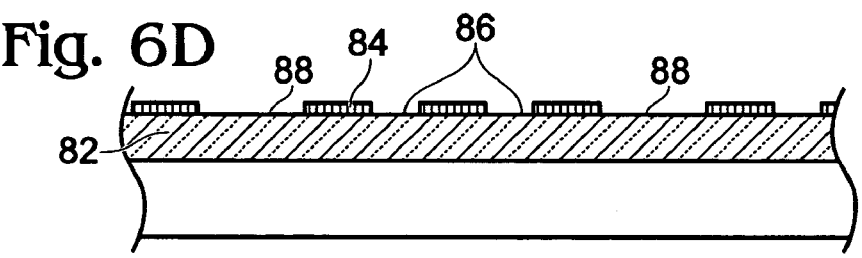

FIG. 6D shows polarizing layer 84 after patterning to define nonpolarizing regions 86. Nonpolarizing regions 86 correspond to regions of localized removal or modification of polarizing layer 84. Such regions may define code elements that form a code or areas that bound code elements. Polarizing layer 84 also may be removed near future particle perimeter 88, for example, to allow polarizing layer 84 to be fully enclosed within the particle in a subsequent step.

Polarizing layer 84 may be patterned using any suitable method, such as photolithography with dry or wet etching, and/or by laser ablation, among others. Since the material of substrate sheet 82 may be chosen to have little absorption of light within the range of wavelengths of polarization of polarizing layer 84, patterning may be effective using a laser having a wavelength within the range of polarization of the polarizing material. Such a laser may direct ablation of the polarizing material that is highly selective and self-stopping in this case. It also may be beneficial to choose material of plate 80 having low absorption of light within the wavelength range of polarization of the polarizing layer 84. As an example, a green laser (LE-100 GB, manufactured by RMI, Lafayette, Colo.), with an output wavelength of 532 nm and output power of 2.5 W, has been found to be effective for patterning Black LCP thin-film polarizing material (Optiva, Inc.), which polarizes light in the 400-700 nm range. The materials of substrate sheet 82 and plate 80 may be selected to be transparent for this wavelength.

Figure 6E:
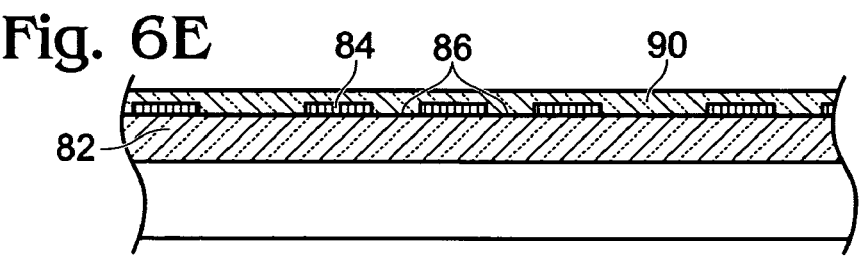

FIG. 6E shows substrate sheet 82 and polarizing layer 84 covered with cladding layer 90. Cladding layer 90 (such as PMMA, PEMA, etc.) may be applied over polarizing layer 84 and nonpolarizing regions 86 by any suitable method, such as laminating a plastic sheet to substrate sheet 82 and/or polarizing layer 84, and/or by drawing liquid material (such as a melted material or a prepolymer solution, among others), followed by drying, solidifying, and/or curing. Cladding layer 90, when applied by a drawdown machine, may define a substantially flat or planar exterior surface due to flowing and filling recessed nonpolarizing regions 86, where polarizing layer 84 has been removed.

Figure 6F:
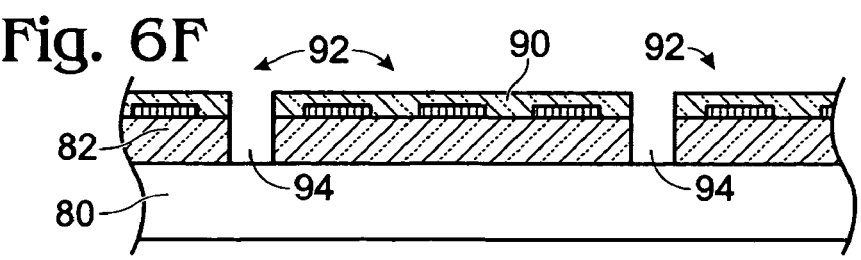

FIG. 6F shows substrate sheet 82 and attached layers after they have been cut to form individual particles 92. Substrate sheet 82 and cladding layer 90 may be cut at regions shown at 94 by any suitable method, including mechanical cutting, chemical etching, and/or with a laser, among others, to provide singulation of individual particles. A $CO_2$ laser with an output wavelength of 10.6 microns and a power of 12 W (Venus Desktop Engraver, ILaserPro, Inc.) may be effective for cutting PMMA or PEMA due, for example, to efficient absorption of light from this laser by these materials. However, plate 80 may be transparent at this same wavelength. Particles 92 may be separated from plate 80 using any suitable method, including mechanically (that is, peeled-off) and/or by soaking in a solvent until they are detached, among others.

Figure 7:
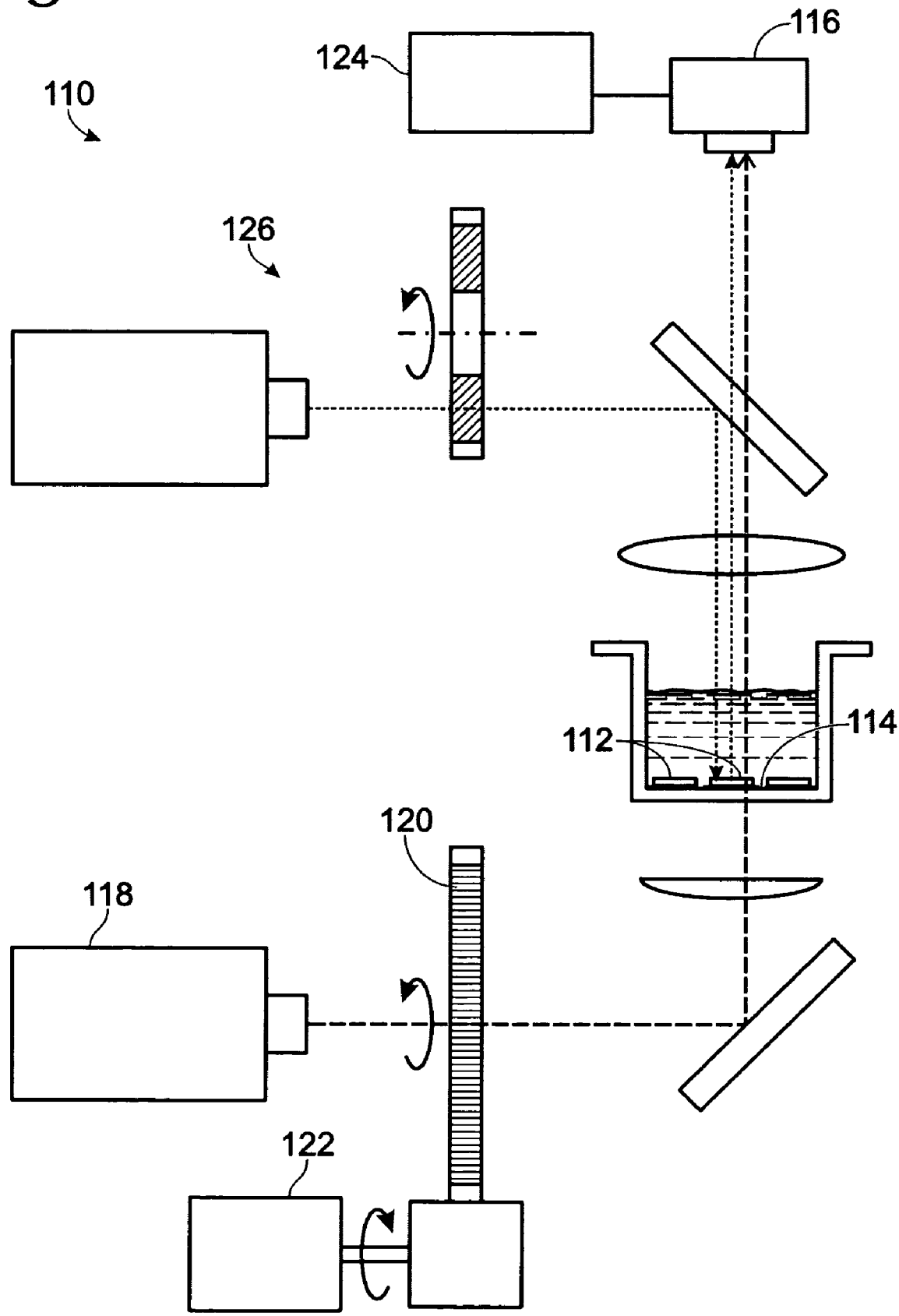
FIG. 7 is a schematic view of a system for measuring polarization codes and assay results, in accordance with aspects of the invention.

FIG. 7 shows an exemplary system 110 for reading polarization codes on particles 112 randomly distributed on a surface 114. System 110 may be used to carry out a method for detecting the codes. The method may include acquiring at least two images of surface 114 and particles 112 using a camera 116 and transmitted light from a light source 118 linearly polarized by a polarizing filter 120. The polarization plane of light during one image acquisition may be substantially nonparallel to the polarization plane of light during another image acquisition. Such changes in the polarization plane may be achieved by altering the polarization of polarizing filter 120, for example, by swinging or rotating the filter using a motor 122 synchronized with camera 116 by a computer/controller 124. In preferred embodiments, the polarization plane of light during one image acquisition is substantially perpendicular to the polarization plane of light during another image acquisition. This may achieve the highest optical contrast. The method also may include combining at least two images of surface 114/particles 112. The step of combining may be carried out by addition or multiplication of the images or by any other suitable mathematical methods of image enhancement. The method also may include recognizing an image of the particle code. Optics 126 may be used to measure a characteristic of samples associated with particles 112, for example, fluorescent signals as shown here.

In some embodiments, a method of detecting polarization codes may include illuminating surface 114 (and randomly oriented particles 112) using linearly polarized light, for which the light polarization plane is rotated with frequency of F revolutions per time unit. Changing the polarization plane of light may be achieved by rotating or otherwise altering polarizing filter 120 with a constant speed of F revolutions per unit time by motor 122. At least two images of surface 114 and particles 112 may be acquired by camera 116 with sequential image acquisitions being spaced by a time interval or increment that is substantially different from $0.5*(1/F)*k$, where k is an integer, and where the asterisk denotes multiplication here and below. This approach may not require synchronization of the camera with orientation of the polarizing filter and may simplify implementation of the method. In preferred embodiments, sequential image acquisitions are performed at time increments that are substantially equal to $0.5*(1/F)*(0.5*n+k)$, where n is the number of the image in the sequence, and k is an integer. This approach may provide the highest optical contrast after combining at least two images of surface 114/particles 112.

In some embodiments, more than two images may be acquired. In this case, subsequent image acquisitions may be performed at time increments that are substantially equal to $0.5*(1/F)*(0.5*n/m+k)$, where n is the sequential number of the image, m is the number of images, and k is an integer. Combination of all m images may provide high optical contrast of the particle codes independent of particle orientation.

Figure 8:
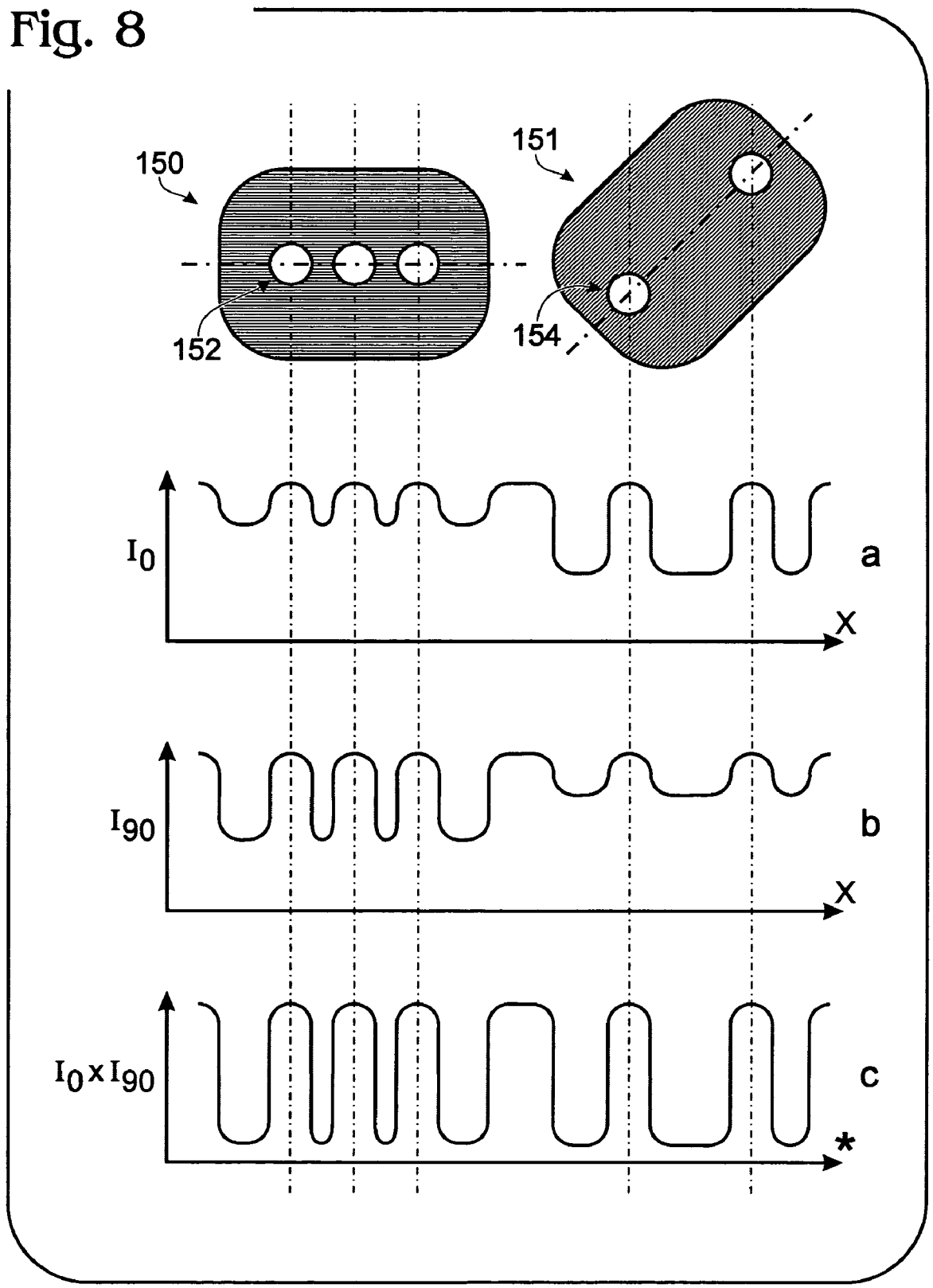
FIG. 8 is a schematic representation of data that may be obtained by illuminating polarization codes on particles using light with different planes of polarization, in accordance with aspects of the invention.

FIG. 8 shows combination of acquired images to achieve high optical contrast. Particles 150, 151 with different codes 152 and 154, respectively, are oriented randomly relative to their planes of polarization. Graphs (a) and (b) show schematic representations of two images that might be acquired for the particles. For simplicity, the images are shown here as one-dimensional distributions of transmitted, linearly polarized light. The light has an intensity (I) from an indicated coding axis or coding plane of each particle defined by the code elements, which has been plotted along the x-axis of each graph. Graph (a) shows intensity $I_0$ as a function of position along the particle coding axis, where intensity has been acquired with a zero-degree orientation of light polarization. With this orientation of polarization and particles, code 152 of particle 150 is only slightly above background, whereas code 154 of particle 151 contrasts more strongly with background. Graph (b) shows intensity $I_{90}$ as a function of position along the particle coding axis, where intensity has been acquired at a ninety-degree orientation of light polarization relative to graph (a). Note how this orientation of polarization produces better contrast for code 152 than code 154. Accordingly, image recognition of the particle codes using only one image, for example, as represented by graph (a) or graph (b), may not be efficient due to low optical contrast of some particle images. Therefore, combining images may improve contrast. For example, graph (c) shows combining the two images of graphs (a) and (b), acquired with different polarization orientation, into one image corresponding to the product of the intensities ($I_0*I_{90}$) as a function of position. This approach may provide equally high optical contrast for every particle, as shown here, and may allow efficient image recognition of all particle codes independent of physical orientation of the particles on a surface.

Combination of two or more images acquired with different orientations of light polarization may allow differentiation between the contrast created by the code and the contrast created by other objects (e.g., debris), even if the latter is higher than the former, assuming that the other objects are nonpolarizing, which typically is the case.

Particles with polarization codes may be used in any suitable assay, with any suitable samples and reagents, and with any suitable detection methods. Exemplary samples include distinct cell populations, and exemplary assays include library screens of candidate cell modulators, such as drug screens. Suitable assays, samples, reagents, and detection methods are described in more detail in the patents and patent applications identified in the Cross-References and incorporated herein by reference, particularly the following U.S. patent applications: Ser. No. 10/120,900, filed Apr. 10, 2002; Ser. No. 10/273,605, filed Oct. 18, 2002; and Ser. No. 10/282,904, filed Oct. 28, 2002.

Selected Embodiments

This section describes selected embodiments of the invention, presented as a series of indexed paragraphs.

1. A particle with an optically recognizable code comprising a substrate, part of which has light polarizing properties in accordance with a code pattern.

2. The particle of paragraph 1, comprising a substrate; at least, one side of the substrate is covered with, at least, one layer of a material with light polarizing properties; a part of the substrate is cleared of the polarizing material in accordance with a code pattern.

3. The particle of paragraph 2, wherein the substrate is made of a material with low light absorption in the wavelength range used for coded particle detection.

4. The particle of any of paragraphs 1-3, wherein the polarizing material is chosen with linear light polarization properties in the light wavelength range used for coded particle detection and low light absorption in the other light wavelength ranges.

5. The particle of any of paragraphs 1-4, comprising, at least, one cladding layer over the polarizing layer.

6. The particle of any of paragraphs 1-5, wherein the cladding layer(s) of material is (are) extended over the part of the substrate cleared of the polarizing layer.

7. The particle of any of paragraphs 1-6, wherein the outer surface of the cladding layer is planarized.

8. The particle of any of paragraphs 1-7, wherein the cladding layer is made of a material with low light absorption in the light wavelength range used for coded particle detection.

9. The particle of any of paragraphs 1-8, comprising the second layer of a material with polarizing properties.

10. The particle of paragraph 9, wherein the second polarizing layer is located over the first cladding layer.

11. The particle of paragraph 9, wherein the second polarizing layer is located over the second side of the substrate.

12. The particle of paragraph 10, wherein the polarizing plane of the second polarizing layer is substantially parallel to the polarizing plane of the first polarizing layer.

13. The particle of paragraph 10, wherein the polarizing plane of the second polarizing layer is substantially perpendicular to the polarizing plane of the first polarizing layer.

14. The particle of any of paragraphs 9-12, wherein a part of the substrate is cleared of the second polarizing layer.

15. The particle of paragraph 14, wherein the pattern of the second polarizing layer substantially coincides with the pattern of the first polarizing layer.

16. The particle of any of paragraphs 9-15, comprising the second cladding layer of material over the second polarizing layer.

17. The particle of paragraph 16, wherein the second cladding layer of material is extended over the part of the substrate cleared of the second polarizing layer.

18. The particle of paragraph 17, wherein the outer surface of the second cladding layer is planarized.

19. The particle of any of paragraphs 16-18, wherein the second cladding layer is of a material with low light absorption in the light wavelength range used for coded particle detection.

20. The particle of any of paragraphs 2-19, wherein a part of the substrate along the substrate edges is cleared of the polarizing material.

21. The particle of any of paragraphs 1-19, wherein at least one polarizing or cladding layer is colored.

22. The particle of any of paragraphs 1-21, wherein the substrate thickness is in the range 0.01-1 mm, the polarizing layer thickness is in the range 0.1-100 microns, and the cladding layer thickness is in the range 1-300 microns.

23. A method of fabrication of a particle with optically recognizable code, comprising the steps of application of, at least, one layer of polarizing material on a substrate and patterning the polarizing layer(s) in accordance with a code pattern.

24. The method of paragraph 23, wherein the substrate material is chosen with low light absorption within the light wave range of polarization of the first polarizing material.

25. The method of paragraph 23 or 24, comprising patterning the polarizing layer(s) by focused light (laser) with the light wavelength within the range of polarization of the polarizing material.

26. The method of any of paragraphs 23-25, comprising removal the polarizing material along the edge of the substrate.

27. The method of any of paragraphs 23-26, wherein two polarizing layers are applied on the first substrate side, the polarization planes of the polarizing layers are oriented parallel to each other.

28. The method of any of paragraphs 23-26, wherein two polarizing layers are applied on the first substrate side, the polarization planes of the polarizing layers are oriented perpendicular to each other.

29. The method of any of paragraphs 23-26, wherein the first polarizing layers is applied on the first substrate side, the second polarizing layers is applied on the second substrate side, the polarization planes of the first and second polarizing layers are oriented parallel to each other.

30. The method of any of paragraphs 23-26, wherein the first polarizing layers is applied on the first substrate side, the second polarizing layers is applied on the second substrate side, the polarization planes of the first and second polarizing layers are oriented perpendicular to each other.

31. The method of any of paragraphs 23-30, comprising the step of application of, at least, one cladding layer over the polarizing layer(s).

32. The method of any of paragraphs 23-28, comprising the steps of: application of the first polarizing layer on the first side of the substrate; patterning of the first polarizing layer; applying the first cladding layer over the first polarizing layer; applying the second polarizing layer; and patterning the second polarizing layer.

33. The method of paragraph 31 or 32, further comprising the step(s) of planarization of the cladding layer(s).

34. The method of paragraph 23, comprising the steps of: fabrication of plurality of substrates as a continuous sheet of the substrate material, application of, at least, one layer of polarizing material on the substrate sheet, patterning of the polarizing layer(s) of every substrate, and singulation of the substrates from each other.

35. The method of paragraph 34, comprising the steps of application of at least one cladding layer before singulation the substrates.

36. The method of any of paragraphs 23, 24, 40, and 41 comprising the steps of forming the substrate(s) by application of a layer of substrate material on a plate before application the first polarizing material, and separation of the substrate(s) from the plate after singulation.

37. The method of paragraph 36, wherein the plate material is chosen with low light absorption within the light wave range of polarization of the polarizing material.

38. The method of paragraph 36 or 37, comprising the step of substrate singulation by a focused light (laser) with a wavelength that provides high light absorption by the substrate material and low light absorption by the plate material.

39. A method of fabrication of a particle with optically recognizable code, comprising the step of patterning a substrate, made of a material with light polarizing properties, by means of localized modification of the substrate light polarizing properties in accordance with a code pattern.

40. The method of paragraph 39, wherein localized modification the substrate light polarizing properties is made by localized substrate material removal.

41. The method of paragraph 39 or 40, wherein localized modification the substrate light polarizing properties is made by changing of polarization orientation and/or randomization and/or, at least partial, destruction of the light polarizing components of the substrate material.

42. The method of any of paragraphs 39-41, comprising the steps of: fabrication Of plurality of substrates as a continuous sheet of the substrate material, localized modification the light polarizing properties of the substrate in accordance with a code pattern for every substrate, and singulation of the substrates from each other.

43. A method of detection of a coded particle among a plurality of coded particles, randomly distributed on a surface, comprising the steps of: acquiring at least two images of the surface with particles using transmitted linearly polarized light, wherein the light polarization plane during every image acquisition is substantially non-parallel to the light polarization plane during another image acquisition, numerical combination of at least two images of the surface, and image recognition of the particle code.

44. The method of paragraph 43, wherein the light polarization plane during every image acquisition is substantially perpendicular to the light polarization plane during another image acquisition.

45. A method of detection of a coded particle among a plurality of coded particles, randomly distributed on a surface, comprising the steps of: illuminating the surface with particles using transmitted linearly polarized light, wherein the light polarization plane is rotated with frequency F revolution per time unit; acquiring at least two images of the surface with particles, wherein the consequent image acquisitions are done with a time increment that is substantially different from $0.5*(1/F)*k$, where k is an integer; numerical combination of at least two images; and image recognition of the particle code.

46. The method of paragraph 45, wherein the consequent image acquisitions are done with the time increment that is substantially equal to $0.5*(1/F)*(0.5*n+k)$, where n is the sequential number of the image, k is integer.

47. The method of paragraph 45, wherein the consequent image acquisitions are done with the time increment that is substantially equal to $0.5*(1/F)*(0.5*n/m+k)$, where n is the sequential number of the image, m is the number of images, k is integer.

48. The particle of paragraphs 1-22 and/or the method of paragraphs 23-47, or any element, limitation, or feature thereof, in combination with any system, device, apparatus, method, assay, kit, or composition, or any element, limitation, or feature thereof, disclosed in any of the patents or patent applications incorporated by reference herein, including but not limited to Ser. No. 10/273,605, filed Oct. 18, 2002.

49. A kit including a particle of paragraphs 1-22 or 48 and/or directed to a method of paragraphs 23-48.

The disclosure set forth above may encompass multiple distinct inventions with independent utility. Although each of these inventions has been disclosed in its preferred form(s), the specific embodiments thereof as disclosed and illustrated herein are not to be considered in a limiting sense, because numerous variations are possible. The subject matter of the inventions includes all novel and nonobvious combinations and subcombinations of the various elements, features, functions, and/or properties disclosed herein. The following claims particularly point out certain combinations and subcombinations regarded as novel and nonobvious. Inventions embodied in other combinations and subcombinations of features, functions, elements, and/or properties may be claimed in applications claiming priority from this or a related application. Such claims, whether directed to a different invention or to the same invention, and whether broader, narrower, equal, or different in scope to the original claims, also are regarded as included within the subject matter of the inventions of the present disclosure.

We claim:

1. A system for performing a multiplexed experiment comprising
a set of particles each comprising a light polarizing material; an optically detectable code, the code of at least two of the particles being distinct; and a substrate; wherein the light polarizing material is distributed on a portion of a substrate surface or embedded within a portion of a substrate surface; and
two or more distinct samples and/or reagents connected to the particles in correspondence with the distinct codes, so that the set of particles can be analyzed in the same multiplexed experiment by identifying samples and/or reagents according to the codes of the respective particles to which the samples and/or reagents are connected.

2. The system of claim 1, wherein a part of the substrate is cleared of the at least one layer of light polarizing material in accordance with a code.

3. The system of claim 2, wherein each code is configured to be recognized in a wavelength range of light, and wherein the substrate has low absorption in the wavelength range.

4. The system of claim 2, wherein the at least one layer of material has linear light polarization capability in the wavelength range of light and low absorption of light in other wavelength ranges.

5. The system of claim 2, wherein each particle includes at east one cladding layer over the at least one layer of material.

6. The system of claim 5, wherein the substrate has a thickness of about 0.01 to 1 mm, wherein the at least one layer of light polarizing material has a thickness of about 0.1-100 microns, and wherein the at least one cladding layer has a thickness of about 1-300 microns.

7. The system of claim 2, wherein the at least one layer of material includes a first layer and a second layer of material each having light polarizing capability.

8. The system of claim 7, wherein each of the first and second layers of light polarizing material defines a respective polarizing plane, and wherein the respective polarizing planes are substantially perpendicular to one another.

9. The system of claim 7, wherein a portion of the substrate is cleared of the second layer of light polarizing material.

10. The system of claim 9, wherein each of the first and second layers of material defines a respective pattern, and wherein the respective patterns substantially coincide.

11. The system of claim 7, wherein each particle includes respective first and second cladding layers disposed over the respective first and second layers of material.

12. The system of claim 1, wherein the particles are connected to distinct populations of biological cells such that distinct code patterns correspond with distinct cell populations.

13. The system of claim 7, wherein each of the first and second layers of light polarizing material defines a respective polarizing plane, and wherein the respective polarizing planes are substantially parallel to one another.

14. The system of claim 1, wherein the particle further comprises an assay portion for performing an assay.

15. The system of claim 14, wherein the assay portion is spatially segregated from the detectable code.

16. The system of claim 14, wherein the assay portion overlaps with the detectable code.

* * * * *